US00PP30787P3

(12) United States Plant Patent
Kordes

(10) Patent No.: US PP30,787 P3
(45) Date of Patent: Aug. 13, 2019

(54) MINIATURE ROSE PLANT NAMED 'KORPOT079'

(50) Latin Name: *Rosa hybrida*
Varietal Denomination: KORpot079

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/732,545

(22) Filed: Nov. 27, 2017

(65) Prior Publication Data

US 2019/0166739 P1 May 30, 2019

(30) Foreign Application Priority Data

Oct. 18, 2017 (QZ) ..... PBR 2017/2618

(51) Int. Cl.
*A01H 5/02* (2018.01)

(52) U.S. Cl.
USPC ..... Plt./117

(58) Field of Classification Search
USPC ..... Plt./117
See application file for complete search history.

(56) References Cited

U.S. PATENT DOCUMENTS

PP16,268 P2 2/2006 Kordes
PP16,918 P2 * 8/2006 Eskelund Hansen ..... Plt./120

* cited by examiner

*Primary Examiner* — Annette H Para
(74) *Attorney, Agent, or Firm* — Buchanan Ingersoll and Rooney PC

(57) ABSTRACT

A new and distinct variety of Miniature Rose Plant, herein referred to by its cultivar name, 'KORpot079', is provided which forms in abundance on a substantially continuous basis attractive, white colored blossoms. The vegetation is vigorous and the growth habit is compact. Attractive ornamental foliage is formed with good disease resistance. The new variety is particularly well suited for providing distinctive ornamentation in the landscape.

2 Drawing Sheets

CROSS-REFERENCE TO RELATED APPLICATIONS

Figure 1:
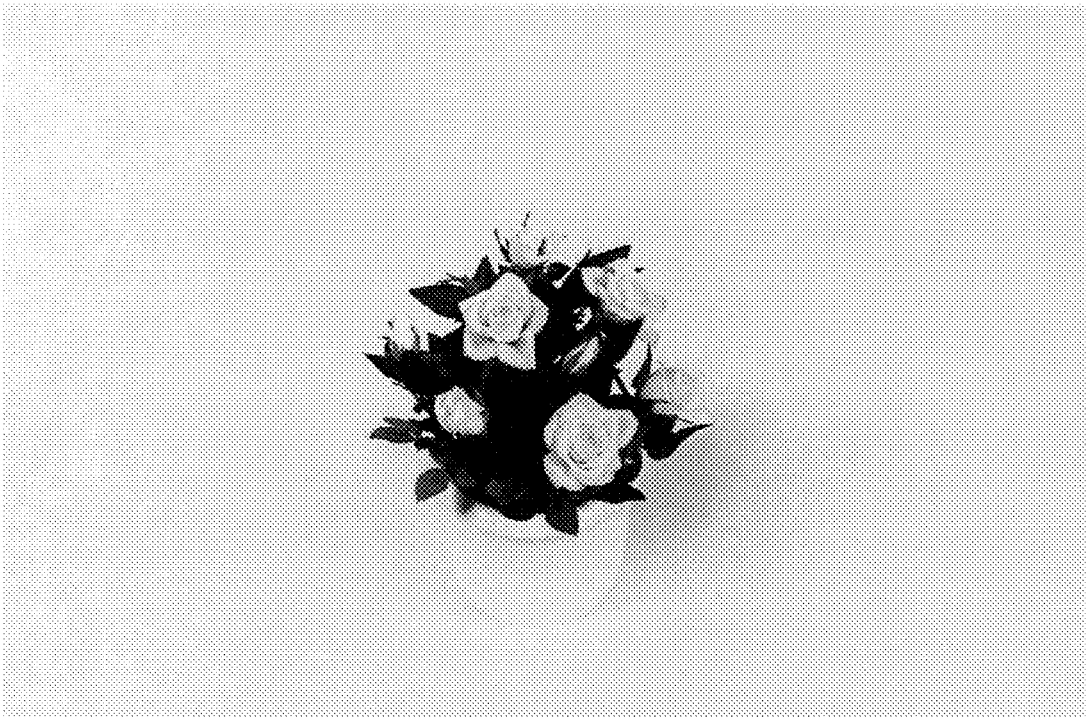

This application claims priority to Plant Breeders' Right Application Number 2017/2618, which was filed at Community Plant Variety Office in the European Union on Oct. 18, 2017, the contents of which are hereby incorporated by reference for all purposes.

Botanical/commercial classification:
Latin name—*Rosa hybrida.*
Common name—Miniature Rose Plant.
Varietal denomination: 'KORpot079'.

SUMMARY OF THE INVENTION

The new variety of *Rosa hybrida* Miniature Rose Plant of the present invention was created during 2013 at Offenseth-Sparrieshoop, Germany by artificial pollination wherein two parents were crossed which previously had been studied in the hope that they would contribute the desired characteristics. The female parent (i.e., seed parent) of the new variety was an unnamed seedling variety (non-patented in the United States). The male parent (i.e., pollen parent) was the 'KORnilsca' variety (U.S. Plant Pat. No. 16,268).

The parentage can be summarized as follows:

unnamed seedling x 'KORnilsca'

The seeds resulting from the above pollination were sown and small plants were obtained which were physically and biologically different from each other. Selective study resulted in the identification of a single plant of the new variety.

It was found that the new Miniature Rose Plant of the present invention possesses the following combination of characteristics:

(a) abundantly and substantially continuously forms attractive, white colored blossoms,
(b) exhibits a compact growth habit,
(c) forms vigorous vegetation, and
(d) forms attractive ornamental foliage with good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the unnamed seedling female parent (i.e., seed parent) displays a lower petal count, a less compact growth habit, and has a different flower color than that of the new variety. Additionally, the 'KORnilsca' variety (i.e., pollen parent) exhibits a different flower color than the new variety and displays solitary flowers, whereas the new variety forms clusters of flowers and has an improved shelf life compared to the 'KORnilsca' variety. Moreover, the new variety can be readily distinguished from similar non-parental varieties. For example, the 'KORpot044' variety exhibits less glossy foliage and larger flower size compared to the new variety. Additionally, the 'Poulpa025' variety exhibits a fragrance and displays approximately 140 petals, whereas the new variety exhibits no noticeable fragrance and displays approximately 90 petals.

The new variety has been found to undergo asexual propagation in Klein Offenseth-Sparrieshoop, Germany by a number of routes such as vegetative cuttings. Asexual propagation techniques in Germany have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot079'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Klein Offenseth-Sparrieshoop, Germany while growing indoors on its own roots in a 6 cm container.

FIG. 1—illustrates a specimen of a plant displaying floral buds and flowers at varying points of opening.

Figure 2:
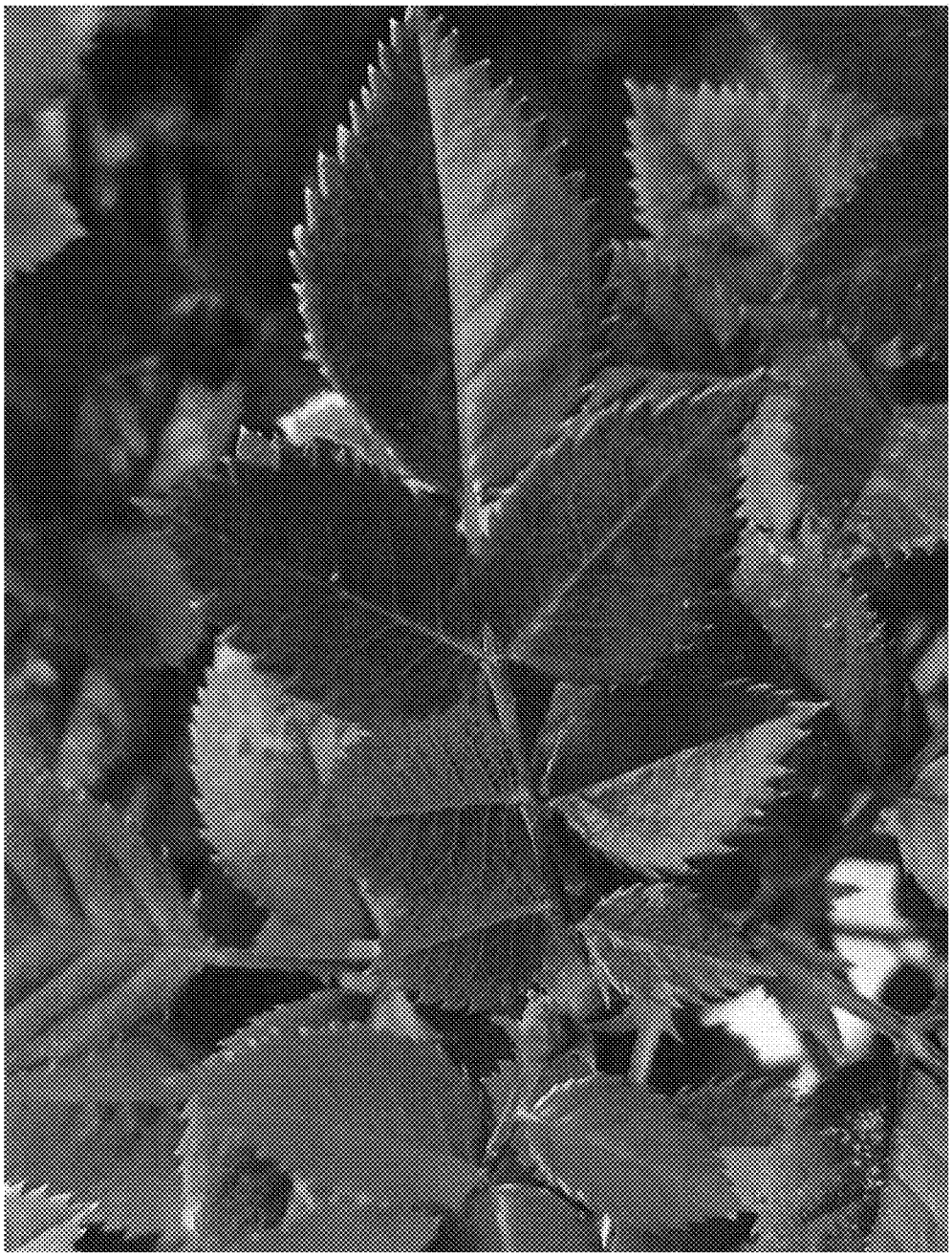

FIG. 2—illustrates a specimen of the foliage—plane view—upper surface.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during July, while growing in a one-gallon container on its own roots at Cochranville, Pa.

Class: Miniature Rose Plant.

Plant:

*Habit*.—Compact and very bushy.

*Height*.—Approximately 12.0 cm on average.

*Width*.—Approximately 20.0 cm on average.

Branches:

*Stem color*.—Commonly near Red Group 46A.

*Main stem length*.—Approximately 7.0 cm on average.

*Secondary stem length*.—Approximately 3.0 cm on average.

*Surface texture stems*.—Glabrous.

*Thorns*.—Young thorns: moderate amount; length is approximately 3.0 mm on average, width is approximately 1.0 mm at point of attachment on average, and color is commonly near Yellow-Green Group N144D. Old thorns: moderate amount; length is approximately 3.0 mm on average, width is approximately 1.0 mm at point of attachment on average, and color is commonly near Greyed-Orange Group N167B.

Foliage:

*General appearance*.—Ornamental with good disease resistance.

*Young foliage*.—Upper surface color: commonly near Green Group 138A. Under surface color: commonly near Green Group 138B.

*Old foliage*.—Upper surface color: commonly near Green Group 137A. Under surface color: commonly near Green Group 137B.

*Petioles*.—Upper surface: texture is smooth, color is commonly near Green Group 137B. Under surface: texture is smooth, color is commonly near Green Group 137C. Length: approximately 1.5 cm on average.

*Rachis*.—Color: upper surface is commonly near Green Group 137B, under surface is commonly near Green Group 137C. Size: length is approximately 4.0 cm on average. Surface texture: smooth with a few small prickles on the under surface.

*Stipules*.—Length: approximately 6.0 mm on average. Width: approximately 3.0 mm on average. Margin: entire to erose. Color: upper surface is commonly near Green Group 137C; under surface is commonly near Green Group 137D.

*Leaf margin*.—Serrate; margin undulation is absent.

*Leaf arrangement*.—Odd pinnate.

Leaflets:

*Number*.—3, 5, and 7.

*Shape*.—Ovate; terminal leaflet apex is acute; and terminal leaflet base is rounded.

*Venation*.—Pattern is reticulate and color is commonly near Green Group 138A.

*Texture*.—Upper surface is glabrous; lower surface is moderately rough.

*Glossiness intensity*.—Upper surface is moderate.

*Size*.—Terminal leaflet: length is approximately 2.5 cm on average and width is approximately 1.5 cm on average. Lower leaflets: length is approximately 1.5 cm on average and width is approximately 1.0 cm on average. 5-Leaflet leaf: length is approximately 4.5 cm on average and width is approximately 3.0 cm on average.

Inflorescence:

*Number of flowers*.—Approximately 12 blooms on average on a plant at once.

*Number of blooms per stem or in a cluster*.—Commonly between 1 and 5 blooms per stem on average.

*Type*.—Solitary inflorescence, sometimes with multiple inflorescences per stem.

*Size*.—Length is approximately 4.0 cm on average; and width is approximately 4.0 cm on average.

*Peduncle*.—Color: commonly Yellow-Green Group 144A. Diameter: approximately 2.0 mm on average. Length: approximately 1.2 cm on average. Surface texture: sparely covered in short, flexible thorns that measure less than 2.0 mm in length.

*Sepals*.—Number commonly 5. Upper surface color and texture: covered in short pubescence and color is commonly near Yellow-Green Group 144A. Under surface color and texture: puberulent and color is commonly near Yellow-Green Group 144B. Size: length is approximately 1.8 cm on average and width is approximately 4.0 mm on average. Shape: lanceolate; apex is acute to aristate. Margin: entire with occasional extensions on two or three sepals measuring approximately 2.0 mm in length and approximately 1.0 mm in width.

*Bud*.—Shape: ovoid to pointed. Size: length is approximately 1.7 cm on average; width is approximately 1.0 cm on average. Color (when opening): commonly near White Group N155A.

*Flower*.—White colored. Form: double, mostly flat. Shape: round. Diameter: approximately 4.0 cm on average. Height: approximately 1.5 cm on average. Duration: commonly on the plant approximately 10 days. Color upon opening: commonly near Orange-White Group 159D with a small basal spot of near Yellow Group 10C. Color after opening: upper and under surfaces are commonly near White Group NN155A blending to Yellow Group 8C at the point of attachment.

*Fragrance*.—None noticeable.

*Petal*.—Number: approximately 90 on average. Drop: good. Length: inner petals are approximately 1.0 cm on average and outer petals are approximately 1.7 cm on average. Width: inner petals are approximately 5.0 mm on average and outer petals are approximately 1.3 cm on average. Shape: overall shape is broadly obovate; apex is round; and base is cuneate. Texture: upper and under surface is glabrous. Margin: entire; margin undulation is weak to moderate.

*Petaloids*.—Number: approximately 3 per flower on average. Color upon opening: commonly near Yellow-Green Group 149D with a small basal spot of near Yellow Group 10C. Color after opening: upper and under surfaces are commonly near White Group NN155A blending to Yellow Group 8C at the point of attachment. Size: length is approximately 8.0 mm on average and width is approximately 4.0 mm on average. Texture: smooth. Margins: variable, entire to erose. Shape: variable, oblong and mostly curving inward; apex is round, and base is cuneate.

*Stamen*.—Number: approximately 20 on average. Anthers: number is about 20 and color is commonly near Yellow-Orange Group 22A; length is approximately 2.0 mm on average. Filaments: length is approximately 1.5 mm on average and color is commonly near Greyed-Yellow Group 160A.

*Pistils*.—General: appear to be underdeveloped and non-viable structures. Number: approximately 40 to 50 on average. Color: commonly near Green Group 142A Size: length is approximately 5.0 mm on average; and width is approximately 1.0 mm on average.

*Receptacle*.—Achenes stand on the bottom and wall; diameter is approximately 5.0 mm on average, shape is round, color is commonly near Yellow-Green Group 144A, and surface texture is smooth.

*Pollen*.—None observed.

*Hips/seed*.—None observed.

Development:

*Vegetation*.—Dark green, vigorous, and strong.

*Blooming*.—Abundant and substantially continuous.

*Winter hardiness*.—Unknown.

*Resistance to disease*.—Good resistance to Powdery mildew, including *Sphaerotheca pannosa*, and *Botrytis* (*Botrytis cinerea*) disease under normal greenhouse growing conditions in Cochranville, Pa. Plants of the 'KORpot079' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) abundantly and substantially continuously forms attractive, white colored blossoms, (b) exhibits a compact growth habit, (c) forms vigorous vegetation, and (d) forms attractive ornamental foliage with good disease resistance;

substantially as herein shown and described.

* * * * *